United States Patent

Yamazaki et al.

[11] 4,128,339
[45] Dec. 5, 1978

[54] AUTOMATICALLY-ADJUSTING PHOTOMETER

[75] Inventors: Yasuhiro Yamazaki, Laguna Niguel; Robert H. Johnson, El Toro; Mark D. McNeil, Irvine, all of Calif.

[73] Assignee: Bio-Dynamics Inc., Indianapolis, Ind.

[21] Appl. No.: 757,352

[22] Filed: Jan. 6, 1977

[30] Foreign Application Priority Data

Aug. 25, 1976 [DE] Fed. Rep. of Germany ....... 2638333

[51] Int. Cl.² ............................................. G01N 21/22
[52] U.S. Cl. ..................................... 356/434; 250/565
[58] Field of Search ............... 356/201, 204, 205, 206; 250/564, 565, 573

[56] References Cited

U.S. PATENT DOCUMENTS

| 3,633,012 | 1/1972 | Wilhelmson | 356/201 |
| 3,917,957 | 11/1975 | Ansevin et al. | 356/201 |
| 3,992,113 | 11/1976 | Egli et al. | 356/206 |

Primary Examiner—John K. Corbin
Assistant Examiner—R. A. Rosenberger
Attorney, Agent, or Firm—Woodard, Weikart, Emhardt & Naughton

[57] ABSTRACT

An automatically-adjusting photometer for measuring the absorbance of a sample in which the amount of light passing through a sample test location is sensed by a photodetector and converted to an electrical output signal. The output signal is amplified and converted to a logarithmic value. Prior to measuring the absorbance of a sample, the photometer is calibrated by a computer. With the sample test location empty, the computer records and places in memory a logarithmic value proportional to the electrical output signal which corresponds to zero absorbance. Next, this value is reduced by a predetermined factor by switching a resistor into the calibration circuitry. The resulting value is also recorded and placed in memory by the computer. When a sample is placed in the test location, the computer records a value proportional to the electrical output signal which corresponds to the absorbance of the sample. Using the three recorded values the computer calculates the correctly-adjusted absorbance of the sample.

8 Claims, 2 Drawing Figures

AUTOMATICALLY-ADJUSTING PHOTOMETER

BACKGROUND OF THE INVENTION

1. Field of the Invention

This invention relates in general to photometric measuring devices and more specifically to a photometer which includes automatic calibration means based on logarithmic value measurement and comparisons.

2. Description of the Prior Art

There are various types of photometric systems associated with measuring the absorbance of a sample. These systems often incorporate manual means for the "zeroing" of the measuring circuit prior to measuring the desired sample. In conventional photometers, there are two adjustment knobs for this manual calibration. One knob is for adjusting the base line for displaying "zero" absorbance for a 100% transmittance signal. The other knob is to set the gain of the amplifier after logarithmic conversion to display a corresponding absorbance for a given transmittance. This is usually determined by inserting a filter or color solution of known absorbance value in the test location.

This conventional method is very cumbersome and it is often difficult to obtain and maintain a filter or solution with an accurately known absorbance value. This will often result in an inaccurate gain slope setting.

Scott, U.S. Pat. No. 3,579,105 discloses a digital measuring circuit for determining a mathematical relationship between a variable signal and a relatively constant "reference" signal. The circuit operates on the theory of supplying a blank input which is expected to be equal to the reference signal. The recalibration circuit causes a change in the amplitude value, as by attenuation, of the reference signal so as to create a balance between the blank signal and the reference signal. Actually, the circuitry of Scott provides, in digital form, the logarithm of the ratio of two electrical inputs and readjusts the function to equal zero when the two inputs are to be considered equal. The adjustment or attenuation factor is stored and then utilized as part of the computing mode to calibrate out any errors. This system still involves the concept of "zeroing" the equipment and thus, the circuitry necessary to accomplish this is extensive and somewhat complicated. Consequently, the Scott system has the disadvantage of being complex and costly. A further disadvantage is that the attenuation factor is a time-dependent variable which compounds the problem of establishing an accurate zero balance. Other U.S. patents showing related photometers and calibrating apparatus are: U.S. Pat. Nos. 2,909,724 to Onksen; 2,942,183 to Chance; 3,377,467 to Staunton et al; 3,535,637 to Goransson; 3,634,868 to Pelavin; 3,711,774 to Bohler; 3,743,429 to Kawai; 3,733,137 to Badessa and 3,818,198 to Walker et al.

SUMMARY OF THE INVENTION

One embodiment of the present invention is an automatically-adjusting photometer for measuring light absorption of a sample including an optical portion, a converting network, a computer, an analog to digital converter, and a display apparatus connected to the output of the computer. The optical portion provides a beam of light through a sample test location which strikes a photodetector. The output of the photodetector is an electrical signal which is conducted to the converting network. The converting network amplifies and computes a logarithmic value proportional to the output signal. The apparatus within the converting network is a resistor combination which reduces the logarithmic value corresponding to the output signal by a predetermined factor. The computer having both calibration and computational modes as well as a memory, places these logarithmic values in memory and then retrieves the stored data for calculation of the absorbance value, A, of a sample which has been placed in the test location. The analog to digital converter converts the data form of the converting network output which is recorded by the computer. The display apparatus is connected to the output of the computer and displays the absorbance value of a sample.

It is an object of this invention to provide an improved method of automatically adjusting a photometer.

Related objects and advantages of the present invention will be apparent from the following description.

DESCRIPTION OF THE PREFERRED EMBODIMENT

Figure 1:
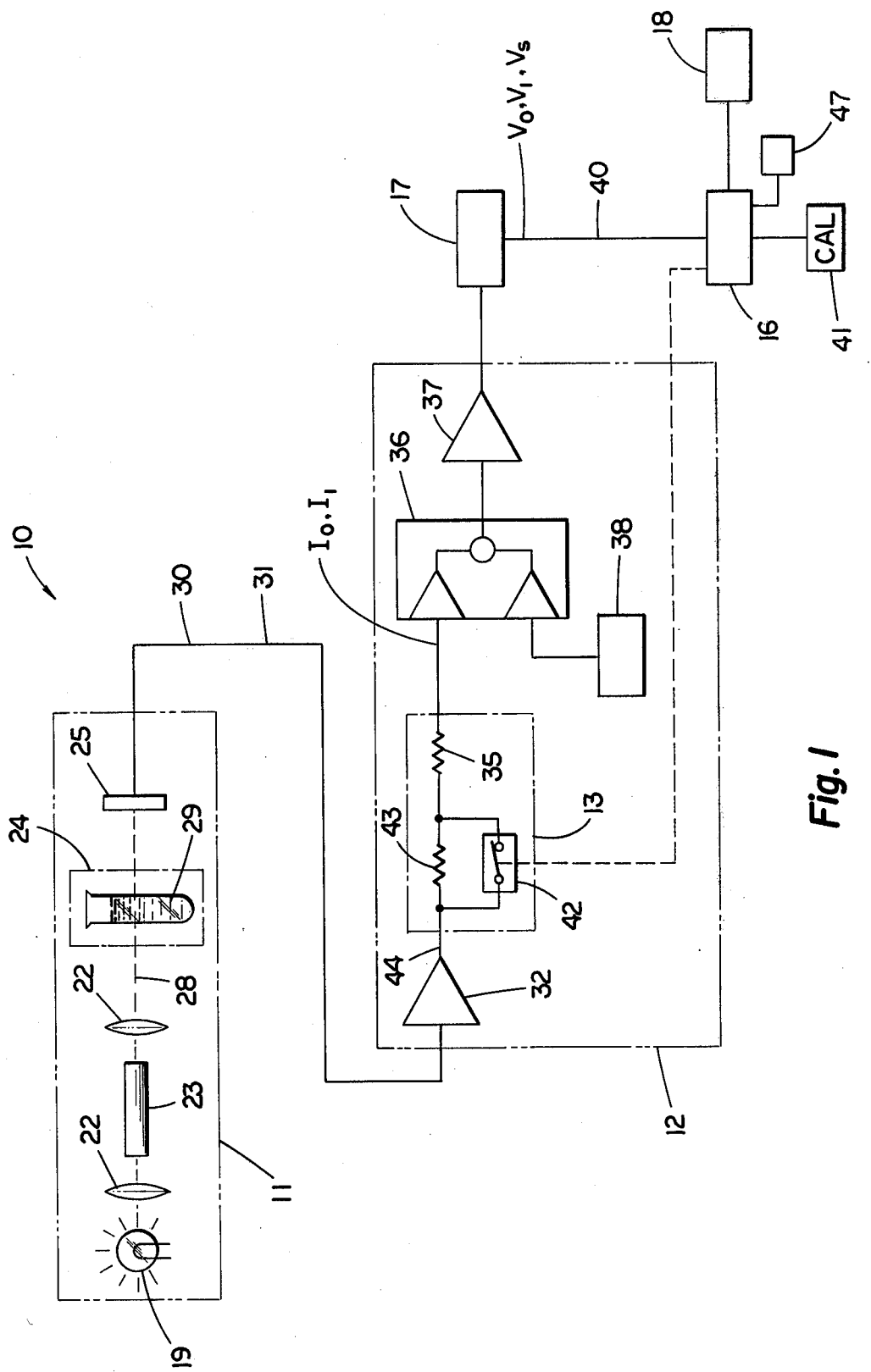
FIG. 1 is a schematic circuit diagram of an automatically-adjusting photometer with a single light beam.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

One embodiment of the present invention, as shown by the schematic circuit diagram of FIG. 1, is an automatically-adjusting photometer 10 with an optical portion 11, converting network 12, resistor and switch network 13, computer 16, analog to digital converter 17 and display apparatus 18.

Optical portion 11 includes a lamp 19, lenses 22, monochromatic filter 23, sample test location 24 and photodetector 25. The beam of light 28 passes from lamp 19 to photodetector 25 going through test location 24 into which a sample 29 is placed. The absorbance value A of sample 29 is to be determined after the photometer 10 has been calibrated. Photodetector 25 transmits an output signal proportional to the intensity of the striking light beam 28. The output signal 30 is conducted to the converting network 12 by coupling 31. Amplifier 32 receives output signal 30 at its input and transmits a corresponding output signal 44 either through switch 42 or resistor 43 and then through resistor 35 to one input of current logarithmic ratio amplifier 36. Since amplifier 36 is a two-input device and in this embodiment there is only one light beam and only one current signal input, a constant current source 38 is electrically connected to the second input of amplifier 36 to provide a constant reference current. The output signal from amplifier 36 is a voltage signal. This signal is further amplified by amplifier 37 and is then converted into digital form by analog to digital converter 17. The resultant output signal 40 from converter 17 is received by computer 16 and can be stored in computer memory 47, displayed by apparatus 18 or both. The photometer 10 will function as described irrespective of the particular sample placed in test location 24.

Of course, different samples may display different absorbance characteristics and thus signal levels in the circuit will differ. The degree of weakening of the light beam intensity by the sample is related to the transmission degree, T, which can assume values between 0 and 1 relative to the particular sample 29. A T value equal to 0 corresponds to complete absorption of the light beam 28 by the sample 29; a T value equal to 1, corresponding to 100% transmission and indicates an unhindered passage of the incident light beam 28. The absorbance, A, of the sample 29 can be determined according to the equation $A = \log 1/T$. Photodetector 25 emits a signal proportional to the transmission degree, T, while amplifier 36 emits a signal linearly proportional to the absorbance, A. A suitable device for amplifier 36 is a Model 756 or 757 manufactured by Analog Devices of Norwood, Massachusetts.

To obtain an accurate reading of the absorbance value of sample 29, it is necessary to calibrate the photometer 10 against some type of reference in order to determine a scaling factor and then mathematically apply this factor to the absorbance reading of a sample. With sample test location 24 empty, calibration switch 41 is depressed by the user. This sends a command signal to the computer 16 and the computer initiates the following pre-defined program sequences comprising the calibration procedure.

A 2-second time loop is activated to allow a brief time interval for the optical and electrical time-constants to settle down. Switch 42 is initially in a normally-closed position grounding resistor 43 and providing a by-pass path to resistor 35. Consequently, the output signal 44 from amplifier 32 will pass only through resistor 35 and have a current signal value of $I_o$ at one input of current logarithmic ratio amplifier 36. The other input of amplifier 36 is electrically connected to the output of constant current source 38.

At the end of the 2-second time loop, the signal at the output of amplifier 37 is a voltage signal which is converted into a digital number, $V_o$, by the analog to digital converter 17. This number, $V_o$, corresponds to a zero absorbance (A) voltage value occurring when the transmission degree (T) is equal to 1 (100% of the incident light passes unabsorbed through the sample test location). This digital number, $V_o$, is stored in the memory 47 of computer 16.

After $V_o$ is read and stored, another 2-second time loop is started and simultaneously switch 42 is opened by computer 16. Opening of switch 42 will remove the by-pass path around resistor 43 and will place resistors 43 and 35 in series. Following the principal of Ohm's Law, the larger resistance will reduce the previous current signal level, $I_o$, at the input of logarithmic amplifier 36, to a lower current signal level value of $I_1$. Signal $I_1$ is amplified by amplifiers 36 and 37 and the corresponding voltage output signal from amplifier 37 is converted into a digital number, $V_1$, by converter 17. $V_1$ is then stored in the memory 47 of computer 16 along with $V_o$ until both $V_o$ and $V_1$ are required for subsequent computational steps.

$V_1$ corresponds to the value of $V_o$ being reduced by a predetermined factor. Although this factor may vary, it is preferred to have $V_1 = 0.1\ V_o$. In order to achieve this mathematical relationship, the ohm value of resistor 43 must be approximately 0.9 times the ohm value of the sum of resistors 43 and 35. With $V_1 = 0.1\ V_o$, the voltage at the output of amplifier 37 corresponding to digital number $V_1$, is equal to a transmission degree (T) of 0.1 and thus according to the equation, $A = \log 1/T$, the value of A is equal to 1. With the measurement and storage of $V_o$ and $V_1$ the routine calibration cycle is ended. With the calibration cycle ended, switch 42 is returned to its normally-closed position and an indicator is then illuminated notifying the user that the photometer is ready for use to measure the absorbance of a particular sample. A sample 29 is then inserted in sample test location 24 and an absorbance measurement button on computer 16 is depressed placing computer 16 in a computational mode. Light beam 28 will pass through sample 29 at which time a portion of the light beam 28 will be absorbed by sample 29. The greater the portion absorbed the lesser the amount of incident light on photodetector 25. The signal amplification and converting will be as described for $V_1$. A third voltage value is read at the output of amplifier 37 and converted into a digital number, $V_s$. The computer 16 then uses $V_s$ along with $V_o$ and $V_1$ to compute the exact absorbance value (A) for the sample 29. The computer uses the equation $A = (V_s - V_o)/(V_1 - V_o)$ to determine A. This equation is derived by expressing the relationship between A and V by means of the equation $A = mV + b$. By applying the initial conditions of $A = 0$ when $V = V_o$ and $A = 1$ when $V = V_1$, the values of m and b can be expressed in terms of $V_1$ and $V_o$. Once A has been computed by the equation $A = (V_s - V_o)/(V_1 - V_o)$ the value of A is displayed by display apparatus 18.

The computer, while in the computational mode, will measure the $V_s$ value once a second, compute and then display the corresponding absorbance value, A, on display apparatus 18. If the absorbance value of another sample is desired, all that is required is to place the sample in the test location 24 and computer 16 will measure a new $V_s$ during the following second and display a corresponding absorbance value.

If it is desired to recalibrate prior to another measurement the values of $V_o$ and $V_1$ can be cleared by depression of switch 41 and the entire sequence will repeat itself. There are several programmable minicomputers which would be suitable for computer 16. One such unit is a Model 4040 manufactured by Intel Corporation of Santa Clara, California.

The same results which have been described are achieved if the measuring signal is a voltage signal and the apparatus reducing the measuring signal by a predetermined factor contains a voltage divider circuit consisting of two resistors, one of which can be grounded in the calibrating procedure by means of switch 42. With such a circuit, logarithmic amplifier 36 would have to be used as a voltage logarithmic ratio amplifier instead of as a current logarithmic ratio amplifier and constant current source 38 would have to be a constant voltage source. However, the remainder of the circuitry would be unchanged.

Figure 2:
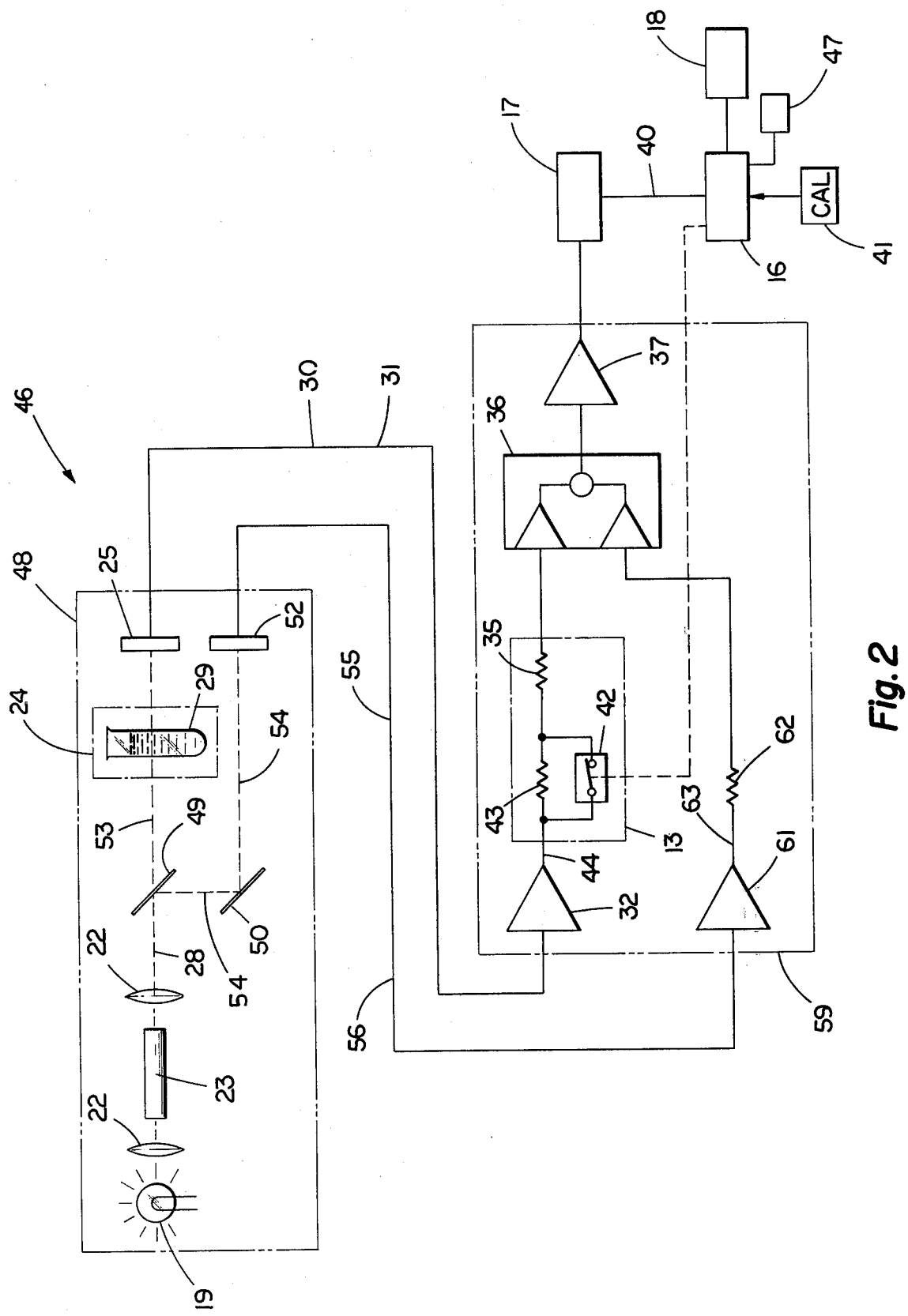
FIG. 2 is a schematic circuit diagram of the FIG. 1 photometer to which a second light beam and associated circuitry have been added.

FIG. 2 shows a further embodiment of the invention which is a split beam photometer 46 whose circuitry and operation are similar to that described for photometer 10 of FIG. 1, the difference being that a second beam of light 54, mirrors 49 and 50 and a second photodector 52, have been added to the new optical portion 48, while amplifier 61 and resistor 62 have been added to new converting network 59. The previous current logarithmic ratio amplifier 36 is the same except that the second input is electrically connected to resistor 62 instead of to constant current source 38. Optical portion 48 has the same elements of optical portion 11 of FIG. 1. However, semi-transparent mirror 49 has been placed in light beam 28 altering the beam in content and direction. Mirror 49 divides light beam 28 into a measuring channel 53 and a reference channel 54. The light of the measuring channel 53 passes through test location 24 and is received by photodetector 25. The light of reference channel 54 initially perpendicular to beam 28 is deflected by mirror 50 and directed to photodetector 52 to a path parallel to beam 53. Photodetectors 25, 52 transmit output signals 30 and 55 which are respectively proportional to the intensity of the incident light beams 53 and 54. Output signals 30 and 55 are conducted to converting network 59 by couplings 31 and 56, respectively. Amplifier 32 transmits output signal 30 as a current signal 44 either through switch 42 or resistor 43 then through resistor 35 to one input of logarithmic amplifier 36. Amplifier 61 transmits output signal 55 as a current signal 63 through resistor 62 to the other input of amplifier 36. Resistors 62 and 35 are equally large and the amplifying factors of amplifiers 32 and 61 are balanced in such a way that fluctuations of intensity of lamp 19 can be eliminated by amplifier 36. Photodetectors 25 and 52 emit signals proportional to the transmission degree T, while amplifier 36 emits a signal linearly proportional to the absorbance A. The measurement of $V_o$, $V_1$ and $V_s$ and the subsequent computation of A for a particular sample, correspond in all respects to the procedure described for the FIG. 1 photometer.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An automatically-adjusting photometer for measuring light absorption of a sample which comprises:
   an optical portion having in combination a light source providing a beam of light, a sample test location, and a photodetector, said light source being constructed to transmit the beam of light through the sample test location so as to strike the photodetector, said photodetector being constructed to transmit an electrical output signal proportional to the intensity of the beam of light;
   converting network means for receiving at an input the electrical output signal and converting said output signal to a logarithmic value;
   said converting network means including means for selectively reducing said output signal by a predetermined factor prior to conversion to a logarithmic value;
   a computer having control and computational modes and a memory portion, said computer in the control mode being constructed to sequentially perform measurment of the logarithmic values of output signals placing these in memory, said computer in the computational mode being constructed to retrieve data stored in memory and calculate the actual absorbance value A of a sample placed in the test location in accordance with the equation $A = (V_s - V_o)/(V_1 - V_o)$ where $V_o$ is the logarithmic value of th output signal occurring when the transmission degree of light through the test location is a known reference value between 0 and 1, $V_1$ is the logarithmic value of the output signal of $V_o$ reduced by said predetermined factor, and $V_s$ is the logarithmic value of the output signal occurring when a sample is placed in the test location;
   an analog to digital converter connecting an output of said converting network means to a computer input; and
   a display apparatus connected to an output of said computer.

2. The photometer according to claim 1 in which, for the computation of $V_o$, the transmission degree of light through said test location equals 1.

3. The photometer according to claim 2 in which the output signal is a voltage signal and the apparatus which reduces the output signal by a predetermined factor is a voltage divider circuit which comprises two resistors, one of which can be bypassed by means of a switch.

4. The photometer according to claim 2 in which the output signal is a current signal and the apparatus which reduces the output signal by a predetermined factor is a resistor and switch network which comprises two resistors through which the current signal flows in series, and a switch connected to one of the resistors and capable of bypassing said one resistor.

5. The photometer according to claim 4 in which the predetermined factor is such that the Vo output signal is reduced by 90%.

6. The photometer according to claim 5 in which said light source is aligned with said photodetector and said sample test location and said sample test location is located directly between said light source and said photodetector.

7. The photometer according to claim 4 in which the computer in its control mode is proportioned and arranged to close the switch of the resistor and switch network when $V_o$ is to be measured and opens the switch when $V_1$ is to be measured.

8. The photometer according to claim 7 in which the optical portion includes a semi-transparent mirror, a deflection mirror, and a second photodetector;
   said converting network including a current logarithmic ratio amplifier having a pair of inputs;
   the semi-transparent mirror being constructed to split the light beam into a sample channel and a reference channel;
   said sample channel passing through the test location prior to striking the first photodetector, said deflection mirror and second photodetector being relatively positioned so that said reference channel strikes said mirror and is deflected thereby striking said second photodetector, the output signals of the two photodetectors corresponding to the two inputs of the current logarithmic ratio amplifier which compares the signals; the logarithmic value output of the converting network being converted from analog to digital form by the analog to digital converter then measured by the computer and presented on the display apparatus.

* * * * *